(12) United States Patent
Tsai et al.

(10) Patent No.: US 10,888,597 B1
(45) Date of Patent: Jan. 12, 2021

(54) COMPOSITION FOR TREATING BRAIN STROKE

(71) Applicant: Enliven Biotechnology Co., Ltd., Taipei (TW)

(72) Inventors: Jaan-Yih Tsai, Taipei (TW); Lin-Yu Tsai, Taipei (TW); Yih-Chih Tsai, Taipei (TW)

(73) Assignee: ENLIVEN BIOTECHNOLOGY CO, LTD., Taipei (TW)

( * ) Notice: Subject to any disclaimer, the term of this patent is extended or adjusted under 35 U.S.C. 154(b) by 0 days.

(21) Appl. No.: 16/519,033

(22) Filed: Jul. 23, 2019

(51) Int. Cl.
| | |
|---|---|
| *A61K 36/236* | (2006.01) |
| *A61K 36/708* | (2006.01) |
| *A61K 36/232* | (2006.01) |
| *A61K 36/539* | (2006.01) |
| *A61K 36/718* | (2006.01) |
| *A61K 36/744* | (2006.01) |
| *A61P 25/00* | (2006.01) |
| *A61K 36/79* | (2006.01) |
| *A61K 36/282* | (2006.01) |
| *A61K 36/355* | (2006.01) |
| *A61K 36/898* | (2006.01) |
| *A61K 9/19* | (2006.01) |
| *A61K 36/258* | (2006.01) |

(52) U.S. Cl.
CPC .............. *A61K 36/236* (2013.01); *A61K 9/19* (2013.01); *A61K 36/232* (2013.01); *A61K 36/258* (2013.01); *A61K 36/282* (2013.01); *A61K 36/355* (2013.01); *A61K 36/539* (2013.01); *A61K 36/708* (2013.01); *A61K 36/718* (2013.01); *A61K 36/744* (2013.01); *A61K 36/79* (2013.01); *A61K 36/898* (2013.01); *A61P 25/00* (2018.01)

(58) Field of Classification Search
None
See application file for complete search history.

(56) References Cited

FOREIGN PATENT DOCUMENTS

| CN | 104862166 | * | 8/2015 |
| CN | 105770200 | * | 7/2016 |

OTHER PUBLICATIONS

Wang, H. et al. Deciphering the Neuroprotective Mechanisms of Bu-Yang Huan-Wu Decoction by an Integrative Neurofunctional . . . . J of Ethnopharmacology 138(1)22-33, Oct. 2011. (Year: 2011).*

* cited by examiner

*Primary Examiner* — Ralph J Gitomer
(74) *Attorney, Agent, or Firm* — Bacon & Thomas, PLLC

(57) ABSTRACT

The present invention provides a method for treating brain stroke, including: administering to a subject in need a composition, including: an extract of a mixture, wherein the mixture includes *Chuanxiong Rhizoma, Rhei Radix et Rhizoma, Angelicae Dahuricae Radix, Scutellaria baicalensis, Coptidis Rhizoma, Gardeniae Fructus*, and *Carica papaya*.

9 Claims, 2 Drawing Sheets

COMPOSITION FOR TREATING BRAIN STROKE

BACKGROUND OF THE INVENTION

1. Field of the Invention

The present invention relates to a composition for treating brain stroke.

2. Description of Related Art

Although the fatality rate of cerebrovascular disease has gradually declined in recent years, cerebrovascular disease ranks fourth in the 10 leading causes of death in Taiwan. Therefore, researchers are dedicated to study the medication with respect to cerebrovascular disease.

Cerebrovascular disease is caused by lesions in the brain blood vessel supplying oxygen and nutrients, resulting in hypoxic necrosis causing neurological dysfunction, which is usually referred as "brain stroke". Generally, the development of brain stroke is rapid, and it results in serious consequences and irreversible damage to a patient if the patient fails to receive a proper treatment at the earliest time, which is the main cause of disability in survivors.

Generally, brain stroke can be classified into three categories: ischemic stroke, hemorrhagic stroke and transient ischemic attack, wherein ischemic stroke is in majority and accounts for 80% brain stroke in Taiwan. It is favorable for brain edema if cerebral ischemia occurs, resulting in increased intracranial pressure, oppressing the blood vessel of peripheral tissues, and thus causing continuous cerebral ischemia. Therefore, brain edema is one of the main reasons for causing fatality after brain stroke occurs.

Nowadays, the medicine for treating acute brain stroke needs to be administered within 3 hours after the onset and used with strict restriction, so that a very limiting number of patients meet the requirements. Besides, the clinical application of the neuroprotective agent remains uncertain because the difficulty in solving the large number of adverse side effects.

Therefore, there is an urgent need to provide a medicine to ameliorate or treat cerebrovascular injury and related symptoms caused by brain stroke.

SUMMARY OF THE INVENTION

In light of this, one object of the present invention is to provide a method for treating brain stroke, which can ameliorate or treat the cerebrovascular injury caused by the brain stroke.

To achieve the aforementioned object, the present invention provides a method for treating brain stroke, comprising: administering to a subject in need a composition, comprising: an extract of a mixture, wherein the mixture comprises *Chuanxiong Rhizoma* (*Ligusticum chuanxiong*, Chuanxiong), *Rhei Radix et Rhizoma* (Rhubarb, Dahuang), *Angelicae Dahuricae Radix* (*Angelica dahurica*, Baizhi), *Scutellaria baicalensis* (Baikal skullcap, Huangqin), *Coptidis rhizoma* (Goldthread rhizome, Huanglian), *Gardeniae Fructus* (Common *Gardenia* Fruit, Zhizi), and *Carica papaya*. In one exemplary embodiment of the present invention, the subject in need is a subject with brain stroke.

In one exemplary embodiment of the present invention, preferably, the mixture comprises 0.5-4 parts by weight of *Chuanxiong Rhizoma*, 1-5 parts by weight of *Rhei Radix et Rhizoma*, 0.5-4 parts by weight of *Angelicae Dahuricae Radix*, 0.5-4 parts by weight of *Scutellaria baicalensis*, 0.05-3 parts by weight of *Coptidis Rhizoma*, 0.05-3 parts by weight of *Gardeniae Fructus*, and 0.1-3.5 parts by weight of *Carica papaya*. More preferably, the mixture comprises 1-3 parts by weight of *Chuanxiong Rhizoma*, 2-4 parts by weight of *Rhei Radix et Rhizoma*, 1-3 parts by weight of *Angelicae Dahuricae Radix*, 1-3 parts by weight of *Scutellaria baicalensis*, 0.1-2 parts by weight of *Coptidis Rhizoma*, 0.1-2 parts by weight of *Gardeniae Fructus*, and 0.5-2.5 parts by weight of *Carica papaya*.

In one exemplary embodiment of the present invention, the mixture may further comprise *Ephedrae Radix et Rhizoma* (Ephedra roots, Mahuang gen), *Panax ginseng* (Korean *ginseng*, Gao li shen), *Kadsurae Radix Cum Caulis* (Hong gu she) *Herba Artemisiae Anomalae* (Diverse Wormwood Herb, Liu ji nu), *Anoectochilus roxburghii*, or a combination thereof.

In one exemplary embodiment of the present invention, preferably, the mixture may further comprise 0.1-3.5 parts by weight of *Ephedrae Radix et Rhizoma*, 1-5 parts by weight of *Panax ginseng*, 0.5-4 parts by weight of *Kadsurae Radix Cum Caulis* (Hong gu she), 0.1-3.5 parts by weight of *Herba Artemisiae Anomalae*, 1-5 parts by weight of *Anoectochilus roxburghii*, or a combination thereof. More preferably, the mixture further comprises 0.5-2.5 parts by weight of *Ephedrae Radix et Rhizoma*, 2-4 parts by weight of *Panax ginseng*, 1-3 parts by weight of *Kadsurae Radix Cum Caulis* (Hong gu she), 0.5-2.5 parts by weight of *Herba Artemisiae Anomalae*, 2-4 parts by weight of *Anoeclochilus roxburghii*, or a combination thereof.

In one embodiment of the present invention, the mixture further comprises *Ephedrae Radix et Rhizoma*, *Panax ginseng*, *Kadsurae Radix Cum Caulis* (Hong gu she), *Herba Artemisiae Anomalae* (Diverse Wormwood Herb, Liu ji nu), and *Anoectochilus roxburghii*.

In one aspect of the present invention, preferably, the mixture further comprises 0.1-3.5 parts by weight of *Ephedrae Radix et Rhizoma*, 1-5 parts by weight of *Panax ginseng*, 0.5-4 parts by weight of *Kadsurae Radix Cum Caulis* (Hong gu she), 0.1-3.5 parts by weight of *Herba Artemisiae Anomalae* (Diverse Wormwood Herb, Liu ji nu), and 1-5 parts by weight of *Anoectochilus roxburghii*. More preferably, the mixture further comprises 0.5-2.5 parts by weight of *Ephedrae Radix et Rhizoma*, 2-4 parts by weight of *Panax ginseng*, 1-3 parts by weight of *Kadsurae Radix Cum Caulis* (Hong gu she), 0.5-2.5 parts by weight of *Herba Artemisiae Anomalae* (Diverse Wormwood Herb, Liu ji nu)s, and 2-4 parts by weight of *Anoectochilus roxburghii*.

In one exemplary embodiment of the present invention, the extract is prepared by the following steps of: (A) providing the mixture; (B) extracting the mixture by heating with water to obtain a crude extract; and (C) filtering the crude extract to obtain the extract.

In one exemplary embodiment of the present invention, a weight ratio of the mixture to the water may be 1:5-30. For example, the weight ratio of the mixture to the water may be 1:6-28, 1:7.5-25, 1:8-23.

However, the present invention is not limited thereto.

In one exemplary embodiment of the present invention, the step (B) comprises: extracting the mixture by heating with water to obtain a first crude extract; filtering the first crude extract to obtain a first filtrate and a first residue; heating the first residue to obtain a second crude extract; filtering the second crude extract to obtain a second filtrate and a second residue; and mixing the first filtrate and the second filtrate to obtain the crude extract.

In one exemplary embodiment of the present invention, the step (C) is: filtering the crude extract to obtain the extract in liquid state.

In one aspect of the present invention, it further comprises a step (D) of drying the extract in liquid state, wherein the step (C) is followed by the step (D). The present invention is not restrictive of the drying method which is used in the step (D). For example, the drying method may be lyophilization, vacuum drying, or hot air drying. In one aspect of the present invention, the extract is dried by lyophilization. The present invention is not restrictive of the method for heating, and it can be implemented in a manner of any know method. For example, direct heating, double-boiling and the like. However, the present invention is not limited thereto.

Herein, treating brain stroke or treatment of brain stroke in the present invention includes ameliorating, alleviating, lowering, and curing the cerebral vascular injury caused by brain stroke. The aforementioned cerebral vascular injury includes brain edema, cerebral infarct, and neuronal apoptosis. However, the present invention is not limited thereto.

In one aspect of the present invention, the method comprises: administering to a subject in need a desired dose of any aforementioned composition for treating brain stroke. The term "desired dose" may be 5-20 ml/kg (administering to a subject in need 5-20 ml/kg of the extract in liquid state), for example, 5-10 ml/kg or 7.5-9 ml/kg. However, the present invention is not limited thereto.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
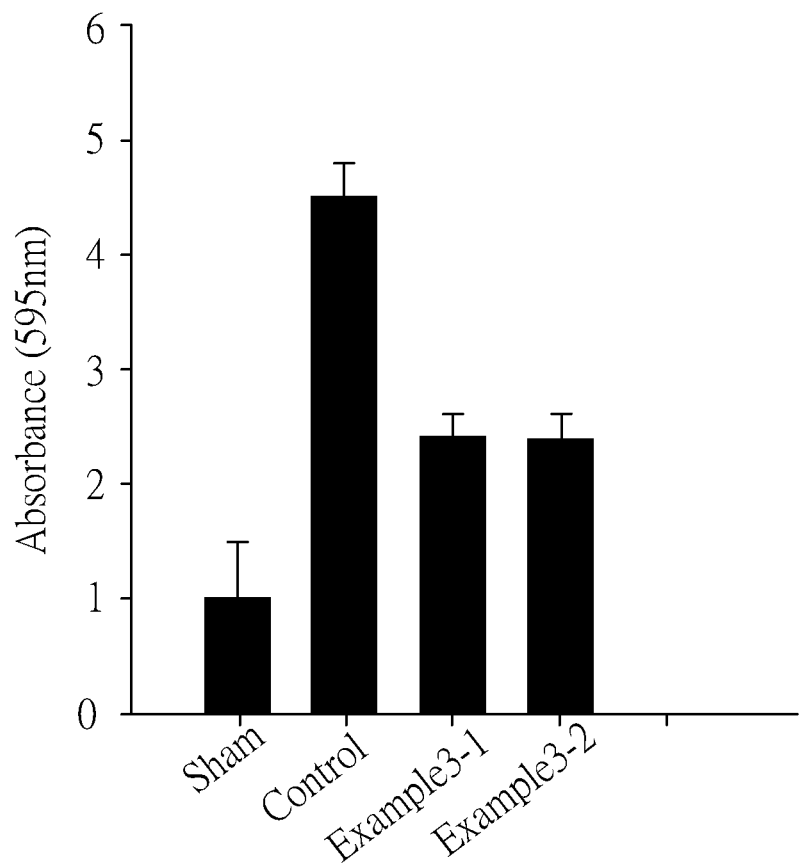
FIG. 1 is a graph showing the brain edema level at 7 days after brain stroke.

<Cell Experiment-1>
Preparation of Composition

A mixture was provided using the ingredients listed in the Table 1 below, then added with water in a weight ratio of 1:11.35 (i.e., the weight ratio of ingredients to water is 1:11.35), and then heating extracted to obtain a first crude extract. The first crude extract was filtered to obtain a first filtrate and a first residue. The first residue was added with water in a weight ratio of 1:8.5 (i.e., the weight ratio of ingredients to water is 1:8.5), and heating extracted to obtain a second crude extract. Afterwards, the second crude extract was filtered to obtain a second filtrate and a second residue. Then, the first filtrate was mixed with the second filtrate to obtain a crude extract, and the crude extract was filtered to obtain an extract, wherein the extract is in a liquid state. Next, the extract was dried by lyophilization, and the obtained product was reserved for subsequent cell experiments. Herein, the numbers in parentheses in Table 1 indicate the parts by weight of each ingredient, and each part by weight is 3.75 grams per part.

TABLE 1

| Embodiments | Ingredients |
| --- | --- |
| Example 1-1 | Chuanxiong Rhizoma (2), Rhei Radix et Rhizoma (3), Angelicae Dahuricae Radix (2), Scutellaria baicalensis (2), Coptidis Rhizoma (1), Gardeniae Fructus (1), and Carica papaya (0.5) |
| Example 1-2 | Chuanxiong Rhizoma (2), Rhei Radix et Rhizoma (3), Angelicae Dahuricae Radix (2), Scutellaria baicalensis (2), Coptidis Rhizoma (1), Gardeniae Fructus (1), Carica papaya (1.5), Ephedrae Radix et Rhizoma (1.5), Panax ginseng (3), and Kadsurae Radix Cum Cauils (2) |
| Example 1-3 | Chuanxiong Rhizoma (2), Rhei Radix et Rhizoma (3), Angelicae Dahuricae Radix (2), Scutellaria baicalensis (2), Coptidis Rhizoma (1), Gardeniae Fructus (1), Carica papaya (1.5), Ephedrae Radix et Rhizoma (1.5), Kadsurae Radix Cum Caulis (2), and Herba Artemisiae Anomalae (1.5) |
| Example 1-4 | Chuanxiong Rhizoma (2), Rhei Radix et Rhizoma (3), Angelicae Dahuricae Radix (2), Scutellaria baicalensis (2), Coptidis Rhizoma (1), Gardeniae Fructus (1), Carica papaya (1.5), Ephedrae Radix et Rhizoma (1.5), Panax ginseng (3), Kadsurae Radix Cum Caulis (2), Herba Artemisiae Anomalae (1.5), and Anoectoehilus roxburghi (3) |
| Comparative Example 1-1 | Ephedrae Radix et Rhizoma (1.5), Panax ginseng (3), Kadsurae Radix Cum Caulis (2), Herba Artemisiae Anomalae (1.5), and Anoectochilus roxburghi (3) |
| Comparative Example 1-2 | Saposhnikoviae Radix (1.5), Ephedra sinica (1), Stephaniae Tetrandrae Radix (1), Ginseng Radix et Rhizoma, Scutellariae Radix (1), Cinnamomi Ramulus (1), Baked Glycyrrhizae Radix et Rhizoma (1), Paeoniae Radix Rubra (1), Chuanxiong Rhizoma (1), Armeniacae Semen Amarum (1), Zingiberis Rhizoma Recens (1), Aconiti Lateralis Radix Praeparata (0.5), Jujubae Fructus (1) |
| Comparative Example 1-3 | Coptidis Rhizoma (3), Scutellariae Radix (2), Phellodendri Chinensis Cortex (2), Gardeniae Fructus (3) |

Minimum Effective Concentration

The PC-12 cell strain was cultured in an RPMI 1640 medium containing 10% HS, 5% FBS and 1% NEAA and in an incubator containing 5% $CO_2$ at 37° C. The bottom of the 96-well plate was coated with poly-L-Lysine Hydrobromide, the liquid was suctioned out after 24 hours. Then the cells were seeded into the plate in a concentration of $8\times10^3$ cells/well after the plate was air-dried in a laminar flow hood, and then cultured for 24 hours to allow the cells to attach the plate. The sample was dissolved to 50 mg/mL in DMSO, and serially diluted to desired concentrations, i.e., 200 µg/mL, 100 µg/mL, 50 µg/mL, 25 µg/mL, 12.5 µg/mL, 6.25 µg/mL, 3.13 µg/mL, and 1.56 µg/mL. A sample with the desired concentration and $Na_2S_2O_4$(5 mM) were added to each well, and the cells are cultured in an incubator at 37° C. for 24 hours. In addition the control group was added with $Na_2S_2O_4$(5 mM) only. After 24 hours, a cell culture medium containing MTS (the ratio of MTS to cell culture solution is 1:10) was added, the reaction was carried out at 37° C. for 1-4 hours, the absorbance at a wavelength of 490 nm was read with an ELISA Reader and the minimum effective concentration was calculated.

Compared with the control group, the lowest concentration having statistical difference was the lowest minimum effective concentration. As shown in Table 2 below, Example 1-2 and Example 1-4 only needed 1.56 µg/mL of the sample to recover the cell viability.

TABLE 21

| Embodiments | Minimum effective concentration (μg/mL) |
|---|---|
| Example 1-1 | 50 |
| Example 1-2 | 1.56 |
| Example 1-3 | 25 |
| Example 1-4 | 1.56 |
| Comparative example 1-1 | 100 |
| Comparative example 1-2 | 25 |
| Comparative example 1-3 | 25 |

<Cell Experiment-2>
Composition Preparation

Compositions for the subsequent cell experiments were prepared with the ingredients listed in the following Table 3 in the same manner as Cell Experiment-1. Herein, the numbers in parentheses in Table 3 indicate the parts by weight of each ingredient, and each part by weight is 3.75 grams per part.

TABLE 3

| Embodiments | Ingredients |
|---|---|
| Example 2-1 | Chuanxiong Rhizoma (2), Rhei Radix et Rhizoma (3), Angelicae Dahuricae Radix (2), Scutellaria baicalensis (2), Coptidis Rhizoma (1), Gardeniae Fructus (1), and Carica papaya (0.5) |
| Example 2-2 | Chuanxiong Rhizoma (2), Rhei Radix et Rhizoma (3), Angelicae Dahuricae Radix (2), Scutellaria baicalensis (2), Coptidis Rhizoma (1), Gardeniae Fructus (1), Carica papaya (1.5), Ephedrae Radix et Rhizoma (1.5), Kadsurae Radix Cum Cauils (2), and Herba Ariemisiae Anomalae (1.5) |
| Example 2-3 | Chuanxiong Rhizoma (2), Rhei Radix et Rhizoma (3), Angelicae Dahuricae Radix (2), Scutellaria baicalensis (2), Coptidis Rhizoma (1), Gardeniae Fructus (1), Carica papaya (1.5), Ephedrae Radix et Rhizoma (1.5), Panax ginseng (3), Kadsurae Radix Cum Caulis (2), Herba Ariemisiae Anomalae (1.5), and Anoectochilus roxburghi (3) |
| Comparative Example 2-1 | Ephedrae Radix et Rhizoma (1.5), Panax ginseng (3), Kadsurae Radix Cum Caulis (2), Herba Artemisiae Anomalae (1.5), and Anoectochilus roxburghi (3) |
| Comparative Example 2-2 | Ephedra sinica (1.5), Cinnamomi Ramulus (1), Ginseng Radix et Rhizoma (1), Angelica sinensis (1), Chuanxiong Rhizoma (1), dried Zingiberis Rhizoma Recens (1), Glycyrrhizae Radix et Rhizoma (1), Armeniacae Semen Rubra (1), Amarum (1), and gypsum |

Recovery Rate of Cell Viability

The PC-12 cell strain was cultured in the same manner as mentioned above, the cells were seeded into the 96-well plate in a concentration of $8 \times 10^3$ cells/well, and then cultured for 24 hours to allow the cells to attach the plate. The sample was dissolved in DMSO, 200 μg/mL of the sample and $Na_2S_2O_4$ (5 mM) were added to each well, and the cells are cultured in an incubator at 37° C. for 24 hours. The comparison group was added with $Na_2S_2O_4$ (5 mM) only, and the control group was free of the sample and $Na_2S_2O_4$. After 24 hours, a cell culture medium containing MTS (the ratio of MTS to cell culture solution is 1:10) was added, the reaction was carried out at 37° C. for 1-4 hours, the absorbance at a wavelength of 490 nm was read with an ELISA Reader and the recovery rate of cell viability was calculated by the following formula: (sample−comparison group)/(control group−comparison group).

As shown in Table 4, the recovery rates of cell viability of Examples ranged from 57.14% to 129.55%, whereas the recovery rates of cell viability of Comparative Examples ranged from 43.18% to 53.41%. It was noted that, the recovery rate of cell viability of Example 2-3 even reached 129.55%, indicating that the composition of the present invention have ameliorating or therapeutic effect on the damaged cells.

TABLE 4

| Embodiments | Recovery rate of cell viability (%) |
|---|---|
| Example 2-1 | 68.75 |
| Example 2-2 | 57.14 |
| Example 2-3 | 129.55 |
| Comparative Example 2-1 | 43.18 |
| Comparative Example 2-2 | 53.41 |

<Animal Experiment>
Composition Preparation

A mixture was provided using the ingredients listed in the Table 5 below, then added with water in a weight ratio of 1:11.35 (i.e., the weight ratio of the ingredients to water is 1:11.35), and then heating extracted to obtain a first crude extract. The first crude extract was filtered to obtain a first filtrate and a first residue. The first residue was added with water in a weight ratio of 1:8.5 (i.e., the weight ratio of ingredients to water is 1:8.5), and heating extracted to obtain a second crude extract. Afterward, the second crude extract was filtered to obtain a second filtrate and a second residue. Then, the first filtrate was mixed with the second filtrate to obtain a crude extract, and the crude extract was filtered to obtain an extract, wherein the extract is in a liquid state.

TABLE 5

| Ingredients |
|---|
| Chuanxiong Rhizoma (2), Rhei Radix et Rhizoma (3), Angelicae Dahuricae Radix (2), Scutellaria baicalensis (2), Coptidis Rhizoma (1), Gardeniae Fructus (1), Carica papaya (1.5), Ephedrae Radix et Rhizoma (1.5), Panax ginseng (3), Kadsurae Radix Cum Caulis (2), Herba Artemisiae Anomalae (1.5), and Anoectochilus roxburghi (3) |

Experimental Animals

In this experiment, the animals were male Sprague-Dawley (SD) rats from BioLASCO Taiwan Co. Seven-week-old rats (245±16 g) were housed in an air-conditioned environment at room temperature of 24±1° C. The light portion (starts at 6 am) of a light-dark cycle accounted for 12 hours, and the dark portion of a light-dark cycle accounted for 12 hours. The rats were free to have food and water without any restriction. Observe whether the physical condition and weight of the rats met the requirement of this experiment. In this experiment, SD rats weighing 300-350 g were selected.

Animal Model of Brain Stroke

A surgical model of middle cerebral artery occlusion (MCAo) was applied in this experiment, which was achieved by inserting sutures into the proximal middle cerebral artery (intraluminal suture technique, also known as suture or filament model). The experimental procedure was described as follows. First, a 4-0 type nylon suture was prepared before the surgery, and its tip was heated to form a spherical shape. After the animals were completely anesthetized (intramuscular injection of Ketamine 44 mg/Kg, and Pentothal 25 mg/Kg was administered by intraperitoneal injection after five minutes), the animals were incised along the middle line of the neck, and the right external carotid artery (ECA) was separated from the internal carotid artery (ICA). Then the ECA was knotted with 4-0 nylon suture to block the blood flow, and the ICA was applied a slipknot using another suture. The ICA was knotted when the MCAo was performed. Afterward, draw a small gap in the ECA near the bifurcation, push the prepared 4-0 type nylon suture forward from the outside of the notch to another branch of the ICA of the common carotid artery, and continually push the suture forward for abound 18-19 mm till encountering a resistance. At this moment, the start point of the middle cerebral artery was occlusive with the tip of the nylon suture, indicating the completion of the middle cerebral artery occlusion surgery.

Dose

The first filtrate and the second filtrate were combined and filtered to obtain a liquid extract of about 500 mL. It was assumed that an adult weighing 60 kg takes one recipe (500 mL) of the liquid extract, and thus the dose was 8.3 ml/kg after calculation.

Experimental Group

The animals were divided into four groups, according to the Table 6 below, for the animal experiment. In addition, the analysis for the subsequent experiments was performed.

TABLE 6

| Embodiments | Experimental design |
| --- | --- |
| Sham operation group | After anesthesia, perform surgery on the animals, but did not block the cerebral blood flood. |
| Control group | After anesthesia, the cerebral blood flow was blocked for 60 minutes, and then reperfused The animals were tube fed with the reverse osmosis water on a daily basis for 7 days. |
| Example 3-1 | After anesthesia, the cerebral blood flow was blocked for 60 minutes, and then reperfused. On the first day after brain stroke, the animals were tube fed with sample (8.3 ml/kg), one dose per day for 7 days. |
| Example 3-2 | After anesthesia, the cerebral blood flow was blocked for 60 minutes, and then reperfused. On the first day after the brain stroke, the animals were tube fed with sample (8.3 ml/kg), two doses per day for 7 days. |

Experimental Steps

The behavioral function was measured one day before the operation, and the result was used as a reference value for the normal state. Ischemic stroke was induced by middle cerebral artery occlusion surgery, and blood supply to the right brain was terminated. The blocking time was 60 minutes leading to ischemia, then the embolization suture was removed, followed by re-supplying the arterial blood flow, and this step was called reperfusion. On the first day after reperfusion, the animals were tube fed with samples or placebo (ie, reverse osmosis water), and measured for the behavior on the daily basis. The animals were sacrificed at 7 days after administration, and the analyses of brain edema, cerebral infarction, and neuronal apoptosis were performed.

Blood Biochemistry Examination

The animal behavior was measured on the $7^{th}$ day of the reperfusion, and the blood was sampled from the heart when the animal was under anesthesia with excessive urethane. Then, a euthanasia was performed on the animal. A portion of the sampled blood was placed in an EDTA anticoagulant tube and mixed well for detection by an automated blood analyzer (Gen. STM, Beckman, USA). Another portion of the sampled blood was placed at room temperature until solidification, then centrifuged to separate the serum, and analyzed by a blood biochemical analyzer (LX-20, Beckman, USA). The analyzed items included: blood urea nitrogen (BUN), creatinine, sodium ion ($Na^+$), potassium ion ($K^+$), serum glutamic oxaloacetic transaminase (S-GOT), serum glutamic pyruvic transaminase (S-GPT), total creatinine kinase (CK-Total), lactate dehydrogenase (LDH), total protein, C-reactive protein/high sensitivity C-reactive protein (CRP/hs-CRP).

Compared with the shame operation group fed with reverse osmosis water, each of the rest groups did not cause significant organ toxicity and did not lead to organ inflammation with respect to the assessment of inflammatory index.

Therefore, the composition of the present invention does not cause toxicity to various organs.

| | Sham operation group | Example 3-1 | Example 3-2 |
| --- | --- | --- | --- |
| BUN | 19.3 ± 1.2 | 18 ± 0.4 | 17 |
| Creatinine | 0.6 | 0.5 | 0.5 |
| Na* | 141.4 ± 1 | 141.5 ± 0.5 | 142.1 |
| $K^+$ | 5.6 ± 0.2 | 7 ± 0.4 | 7 ± 0.6 |
| S-GOT | 157.7 ± 43.2 | 132.8 ± 13.7 | 115 ± 14 |
| S-GPT | 78.7 ± 10.8 | 67.8 ± 7.9 | 55.5 ± 2.5 |
| CK-Total | 1172 ± 925.7 | 1023.5 ± 200.2 | 846 ± 381 |
| LDH | 538 ± 411.8 | 702.7 ± 34 | 458.8 ± 76.5 |
| Total Protein | 5.3 ± 0.1 | 5.5 ± 0.1 | 5.6 ± 0.2 |
| CRP/hs-CRP | <0.2 | <0.3 | <0.4 |

Analysis of Brain Edema

The integrity of the blood-brain barrier was assessed by the amount of vascular leakage after Evans blue combined with albumin in the blood. At 72 hours and 7 days after ischemia reperfusion, the animals were sacrificed under deep anesthesia (Urathane, 500 mg/m; Sigma-Aldrich, USA) followed by administering 2% Evans blue (4 ml/kg; Sigma-Aldrich, USA) to the animal via the femoral vein, and systemic circulation of which was carried on for 2 hours (macroscopic discoloration covering the animals' entire body). Then, the heart was perfused with 50 IU of Heparin (Sigma-Aldrich, USA) until the liquid effluent was a clear liquid. Afterward, the brain tissue was collected, categorized into left and right brain regions (macroscopic Evans blue staining was observed in the infarct area), weighed and placed in a centrifuge tube for grinding. The ground brain tissue was mixed with Formamide in a ratio of 5:1 and placed in an oven overnight. On the next day, the mixture was centrifuged (3500 rpm, 30 minutes) by a centrifuge; then the supernatant was placed in a 96-well plate, the absorbance was measured, by a spectrophotometer at a wave length of 595-650 nm, and the results was quantified, as shown in FIG. 1.

FIG. 1 is a graph showing the brain edema level at 7 days after brain stroke. As shown in FIG. 1, it could be found from the quantification results measured by the spectrophotometer at a wavelength of 595 nm that the brain edema levels of rats for Example 3-1 and Example 3-2 significantly decreased compared with the control group. In details, the brain edema levels of rats for Example 3-1 and Example 3-2 were reduced by about 47%, and there was no significant difference between that the Example 3-1 and Example 3-2. In light of this, the composition of the present invention can alleviate the brain edema level caused by brain stroke.

Figure 2:
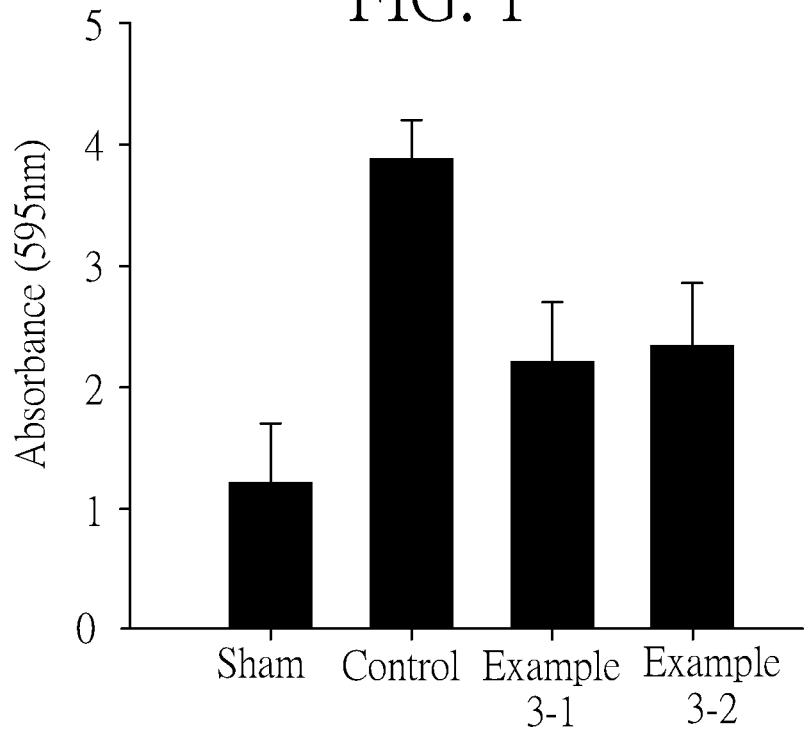
FIG. 2 is a graph showing the brain edema level at 72 hours after brain stroke.

In addition, when the observation time point was advanced to 3 days (i.e., 72 hours, seen as an acute phase of brain stroke) after the brain stroke, the brain edema levels of rats of Example 3-1 and Example 3-2 were respectively reduced by 44% and 40% compared to that of control group. The results were shown in FIG. 2.

Analysis of the Brain Tissue for Infarction Level

After the brain tissue was taken out, the coronal sections were taken at a thickness of 1 mm, and stained with TTC (2,3,5-Triphenyltetrazolium chloride; Sigma-Aldrich, US) solution for 30 minutes. If the cells were alive, it meant that the mitochondria functioned normally, and the dehydrogenase of which normally functioned to take the TTC into the cell, so that the brain tissue was in dark red (or bright red). If the cells were dead, the dehydrogenase malfunctioned, so that the brain tissue was in white. The area of the brain was calculated by the PC-based Image tools software, and each brain slice was calculated for the infarction area. The unstained area was defined as the ischemic lesion, and the infarction volume was obtained by 1 mm (the thickness of each slice)×infarction area of all the slices [mm$^2$]. In addition to the calculation of the infarction volume, there was a need to calculate the entire volume of the ipsilateral hemi-brain. A relative cerebral infarction volume was obtained from the calculated entire volume of the ipsilateral hemi-brain and the infarction volume using the formula below.

$$CIV=[LT-(RT-RI)]\times d$$

LT: left hemisphere
RT: right hemisphere
RI: infarcted area
d: slice thickness (1 mm)

Figure 3:
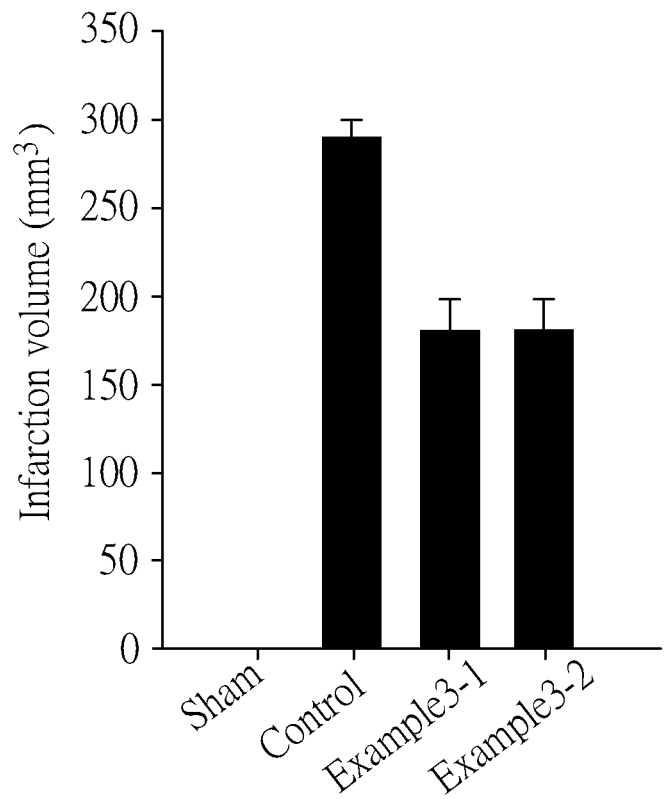
FIG. 3 is a graph showing the brain infarction volume at 7 days after brain stroke.

The calculated cerebral infarction volume was represented by a histogram. As shown in FIG. 3, the cerebral infarction volume of the control group is about 290 mm$^3$. Compared to the control group, both of the Example 3-1 and Example 3-2 could significantly reduce the cerebral infarction volume by 36%. As a result, the composition of the present invention can effectively reduce the infarction volume caused by the brain stroke in rats.

Neuronal Cell Apoptosis Analysis

Terminal deoxynuleotidyl Transferase Biotin-Dutp Nick End Labeling (TUNEL assay, model: 630108, Clontech, USA) was used to detect cell apoptosis in this experiment. During cell apoptosis, DNA cleaved to form nicks or a fractured DNA fragments with 3'-OH ends. The specific nucleotide with a fluorescent dye labeled the 3'-end of the DNA fragments, rendering the cells green, thereby indicating cell apoptosis. In addition, a neuronal marker antibody (Anti-NeuN antibody-Neuronal Marker, catalog number: ab104225, Abcam, USA) and a nuclear marker (DAPI Nucleic Acid Stain, catalog number: D1306, Invitrogen, USA) were added for distinguishing whether the apoptotic cell was a neuron and confirming, by DAPI staining, the position of the fluorescent marker was inside the cell. Therefore, the possibility of staining errors was excluded. The experimental procedure was as follows. First, the slides were immersed in 4% paraformaldehyde/PBS for 15 minutes. The slides were taken out and placed in a staining box, added with an appropriate amount of 1×PBS, and the reaction was carried out in a shaker for 5 minutes 3 times. Then, proteinase K solution (20 µg/ml) was added, and the reaction was carried out at room temperature for 5 minutes. The slides were taken out and placed in a staining box, added with an appropriate amount of 1×PBS, and the reaction was carried out in a shaker for 5 minutes 2 times. The slides were immersed in 4% paraformaldehyde/PBS for 5 minutes. Then, the slides were taken out and placed in a staining box, added with an appropriate amount of 1×PBS, and the reaction was carried out in a shaker for 5 minutes 2 times. Afterward, Equilibration Butter was added, and the reaction was carried out at room temperature for 10 minutes. Then, 45 µl of Equilibration Butter, 5 µl of Nucleotide Mix, and 1 µl of TdT Enzyme were added, and the staining box was placed in a 4° C. refrigerator overnight. The box was then taken out and placed at room temperature for 10 minutes, so that the temperature thereof increased. The slides were immersed in 2×SSC for 15 minutes.

The slides were taken out and placed in a staining box, added with an appropriate amount of 1×PBS, and the reaction was carried out in a shaker for 5 minutes for 3 times. After the liquid on the slide was dried, a few drops of the mounting solution were dropped on the cover slip, and the cover slip was disposed on the slide, in which bubbles between the cover slip and slip were expelled by using a tip. The pictures of the slides were taken at room temperature in the dark. Analysis of brain regions included: frontal cortex (Cortex-M1), parietal cortex (Cortex-PtA), striatum (Striatum-CPu), hippocampus, hypothalamus, cerebellum and brainstem. Cells labeled with NeuN+TUNEL+DAPI triple fluorescence were called apoptotic cells.

Figure 4:
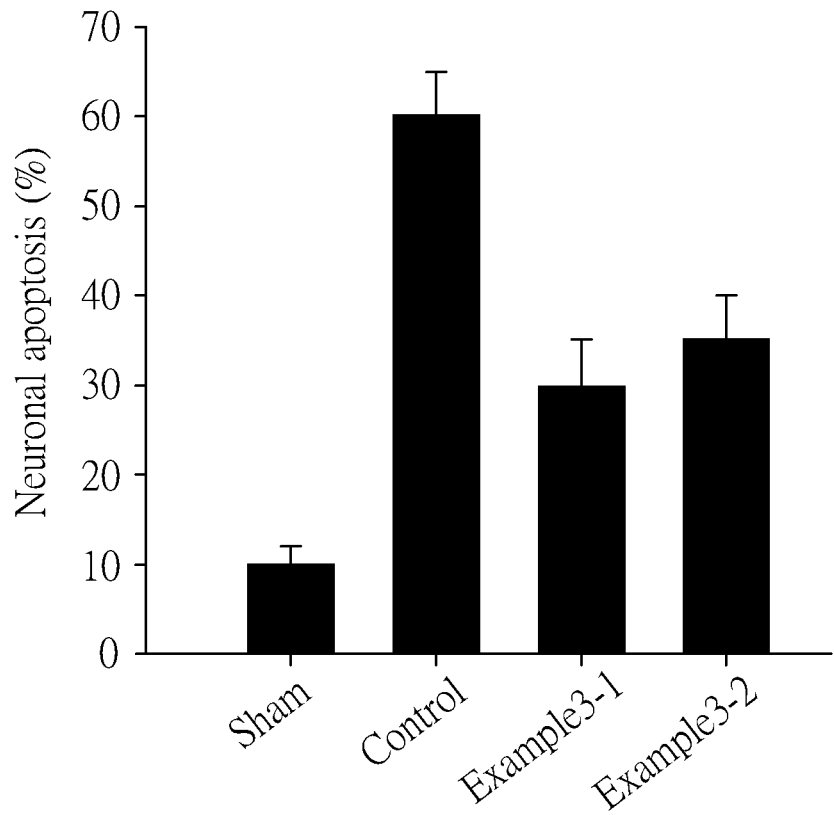
FIG. 4 is a graph showing the neuronal apoptosis in the four brain regions.

It was shown in the experimental results that the control group had significant neuronal apoptosis in the frontal cortex, parietal cortex, striatum, hippocampus, hypothalamus, cerebellum and brain stem at 7 after brain stroke. However, the neuronal apoptosis were significantly reduced in the frontal cortex, parietal cortex, striatum, hippocampus, hypothalamus, and cerebellum of rats given the composition of the present invention. The neuronal apoptosis was significantly reduced in the frontal cortex, parietal cortex, striatum, and hippocampus of Example 3-1. In addition, the neuronal apoptosis was significantly reduced in the frontal cortex, parietal cortex and striatum of Example 3-2. All the neuronal apoptotic cells (NeuN+TUNEL+DAPI positive cells) in the seven brain regions are counted, and the statistical results are shown in FIG. 4. Compared to the control group, the neuronal apoptosis in rats given the composition of the present invention can be reduced by 50%, indicating that the composition of the present invention can inhibit or slow down neuronal apoptosis after brain stroke.

Although the present invention has been explained in relation to its preferred embodiment, it is to be understood that many other possible modifications and variations can be made without departing from the spirit and scope of the invention as hereinafter claimed.

What is claimed is:

1. A method for treating ischemic brain stroke, comprising:
    administering to a subject in need thereof an effective amount of a composition, comprising:
    an extract of a mixture,
    wherein the mixture comprises *Chuanxiong Rhizoma, Rhei Radix et Rhizoma, Angelicae Dahuricae Radix, Scutellaria baicalensis, Coptidis Rhizoma, Gardeniae Fructus*, and *Carica papaya*.

2. The method according to claim 1, wherein the mixture comprises 0.5-4 parts by weight of *Chuanxiong Rhizoma*, 1-5 parts by weight of *Rhei Radix et Rhizoma*, 0.5-4 parts by weight of *Angelicae Dahuricae Radix*, 0.5-4 parts by weight of *Scutellaria baicalensis*, 0.05-3 parts by weight of *Coptidis Rhizoma*, 0.05-3 parts by weight of *Gardeniae Fructus*, and 0.1-3.5 parts by weight of *Carica papaya*.

3. The method according to claim 2, wherein the mixture comprises 1-3 parts by weight of *Chuanxiong Rhizoma*, 2-4 parts by weight of *Rhei Radix et Rhizoma*, 1-3 parts by weight of *Angelicae Dahuricae Radix*, 1-3 parts by weight of *Scutellaria baicalensis*, 0.1-2 parts by weight of *Coptidis Rhizoma*, 0.1-2 parts by weight of *Gardeniae Fructus*, and 0.5-2.5 parts by weight of *Carica papaya*.

4. The method according to claim 1, wherein the mixture further comprises *Ephedrae Radix et Rhizoma, Panax ginseng, Kadsurae Radix Cum Caulis, Herba Artemisiae Anomalae, Anoectochilus roxburghii*, or a combination thereof.

5. The method according to claim 4, wherein the mixture further comprises 0.1-3.5 parts by weight of *Ephedrae Radix et Rhizoma*, 1-5 parts by weight of *Panax ginseng*, 0.5-4 parts by weight of *Kadsurae Radix Cum Caulis*, 0.1-3.5 parts by weight of *Herba Artemisiae Anomalae*, 1-5 parts by weight of *Anoectochilus roxburghii*, or a combination thereof.

6. The method according to claim 5, wherein the mixture further comprises 0.5-2.5 parts by weight of *Ephedrae Radix et Rhizoma*, 2-4 parts by weight of *Panax ginseng*, 1-3 parts by weight of *Kadsurae Radix Cum Caulis*, 0.5-2.5 parts by weight of *Herba Artemisiae Anomalae*, 2-4 parts by weight of *Anoectochilus roxburghii*, or a combination thereof.

7. The method according to claim 1, wherein the mixture further comprises *Ephedrae Radix et Rhizoma, Panax ginseng, Kadsurae Radix Cum Caulis, Herba Artemisiae Anomalae*, and *Anoectochilus roxburghii*.

8. The method according to claim 7, wherein the mixture further comprises 0.1-3.5 parts by weight of *Ephedrae Radix et Rhizoma*, 1-5 parts by weight of *Panax ginseng*, 0.5-4 parts by weight of *Kadsurae Radix Cum Caulis*, 0.1-3.5 parts by weight of *Herba Artemisiae Anomalae*, and 1-5 parts by weight of *Anoectochilus roxburghii*.

9. The method according to claim 8, wherein the mixture further comprises 0.5-2.5 parts by weight of *Ephedrae Radix et Rhizoma*, 2-4 parts by weight of *Panax ginseng*, 1-3 parts by weight of *Kadsurae Radix Cum Caulis*, 0.5-2.5 parts by weight of *Herba Artemisiae Anomalae*, and 2-4 parts by weight of *Anoectochilus roxburghii*.

\* \* \* \* \*